United States Patent
Dschietzig (10) Patent No.: US 10,226,512 B2
(45) Date of Patent: Mar. 12, 2019

(54) METHOD FOR TREATING HEART FAILURE WITH PRESERVED EJECTION FRACTION BY ADMINISTERING HUMAN RELAXIN-2

(71) Applicant: Relaxera Pharmazeutische Gesellschaft mbH & Co. KG, Bensheim (DE)

(72) Inventor: Thomas B. Dschietzig, Berlin (DE)

(73) Assignee: Relaxera Pharmazeutische Gesellschaft mbH & Co. KG, Bensheim (DE)

( * ) Notice: Subject to any disclaimer, the term of this patent is extended or adjusted under 35 U.S.C. 154(b) by 0 days.

(21) Appl. No.: 15/313,517

(22) PCT Filed: May 26, 2015

(86) PCT No.: PCT/EP2015/061554
§ 371 (c)(1),
(2) Date: Nov. 22, 2016

(87) PCT Pub. No.: WO2015/177378
PCT Pub. Date: Nov. 26, 2015

(65) Prior Publication Data
US 2017/0182127 A1    Jun. 29, 2017

(30) Foreign Application Priority Data
May 23, 2014 (EP) .................... 14169711

(51) Int. Cl.
*A61K 38/22* (2006.01)
*A61P 9/04* (2006.01)
*A61K 9/00* (2006.01)
*A61K 9/113* (2006.01)
*C07K 14/64* (2006.01)

(52) U.S. Cl.
CPC .......... *A61K 38/2221* (2013.01); *A61K 9/006* (2013.01); *A61K 9/0019* (2013.01); *A61K 9/113* (2013.01); *A61P 9/04* (2018.01); *C07K 14/64* (2013.01)

(58) Field of Classification Search
None
See application file for complete search history.

(56) References Cited

U.S. PATENT DOCUMENTS

2013/0116181 A1    5/2013 Unemori et al.

OTHER PUBLICATIONS

J. Vitovec et al., "New Possibilities for Heart Failure and Hypertension Therapy." XP009180321, Cardiology Review. 2013, (Abstract).

*Primary Examiner* — Zachary C Howard
(74) *Attorney, Agent, or Firm* — Blank Rome LLP (57) ABSTRACT

A pharmaceutical composition for treatment of persons afflicted of heart failure with preserved ejection fraction (HFPEF), diastolic heart failure (DHF) or diastolic dysfunction (DF), the composition comprising a therapeutically effective amount of a compound capable of specific binding to the relaxin receptor (RXFP1) present on fibroblasts, fibromyoblasts, endothelial cells, endocardial cells, and cardiomyocytes in the cardiac muscle to increase the heart's stroke volume at lower end-diastolic pressure.

10 Claims, 5 Drawing Sheets
Specification includes a Sequence Listing.

SEQUENCE LISTING

```
<160> NUMBER OF SEQ ID NOS: 2

<210> SEQ ID NO 1
<211> LENGTH: 24
<212> TYPE: PRT
<213> ORGANISM: Homo sapiens

<400> SEQUENCE: 1

Glu Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 2
<211> LENGTH: 29
<212> TYPE: PRT
<213> ORGANISM: Homo sapiens

<400> SEQUENCE: 2

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25
```

METHOD FOR TREATING HEART FAILURE WITH PRESERVED EJECTION FRACTION BY ADMINISTERING HUMAN RELAXIN-2

FIELD OF THE INVENTION

The present invention relates to methods and compositions for treating human subjects afflicted with heart failure.

BACKGROUND OF THE INVENTION

Heart failure is commonly classified based on which heart function or which side of the heart is most affected. Left-sided heart failure describes a failure of the left-sided pumping action by which oxygen-rich blood from the lungs is moved through the left atrium into the left ventricle and then out into the rest of the body. The term right-sided heart failure is used for a failure of the right-sided pumping action which pumps blood that returns to the heart through the veins through the right atrium into the right ventricle and then back out into the lungs to have it replenished with oxygen. The symptoms of heart failure are further distinguished whether they have developed quickly (acute heart failure) or gradually over time (chronic heart failure). Congestive heart failure (CHF) describes the general condition in which the heart cannot pump enough blood to meet the needs of the body. As blood flow out of the heart slows, blood returning to the heart through the veins backs up, causing congestion in the tissues. Typical signs thereof are swollen legs or ankles, tiredness, difficulties of breathing, pulmonary edema, respiratory distress. CHF may be caused by coronary artery diseases, congenital and primary heart diseases, infections of the heart muscle (cardiomyopathy, endocarditis and/or myocarditis), myocardial infarctions, high blood pressure, heart valve diseases. CHF also affects the function of the kidneys. The drugs used in treatment of CHF are angiotensin inhibitors and vasodilators to expand blood vessels and decrease resistance, beta blockers to improve the function of the left ventricle, digitalis to increase the pumping action of the heart and diuretics for an elimination of excess salt and water.

The present disclosure relates to heart failures with preserved ejection fraction (HFPEF), also named heart failure with normal ejection fraction or simply diastolic heart failure (DHF), and more specifically to a HFPEF subgroup involving altered chemo-mechanical properties of the heart muscle proteins. Diastole is that phase of the cardiac cycle when the heart is not contracting to propel blood out (systole) to the body, brain and lungs but instead is relaxing and filling with incoming blood that is being returned from the body through the inferior vena cava (IVC) and through the superior vena cava (SVC). The HFPEF subgroup of heart failures is therefore associated with a decline in diastolic performance of the left ventricle of the heart. When the cardiac muscle has become stiff and lost its ability to relax the left ventricle is not readily filled with blood following contraction and the cardiac output becomes either diminished or an elevated ventricular diastolic pressure despite essentially normal end diastolic volume (EDV) is observed for compensation. The HFPEF is often characterized histologically by a hypertrophy of cardiomyocytes, increased interstitial collagen deposition and calcium deposition within the myocardium which are assumed to lead collectively to decreased distensibility and compliance. The chemo-mechanical characteristics of the heart muscle proteins as well as myocytes and the biophysics of the failing heart have not yet achieved clinical relevance.

There is no specific treatment of HFPEF available. When the chronic condition is tolerable by the patient, the therapy may be directed at aggravating factors such as high blood pressure and diabetes. Diuretics are often given. The administration of calcium channel and/or angiotensin II receptor blocker drugs may be of benefit in reducing ventricular stiffness in some cases but there is no favorable effect in mortality rates. A major complication is pulmonary edema the treatment of which by diuretics is often challenging since the stiffened heart and vessels of the patients are very susceptible to hypotensive events after salt and water excretion. Thus, there are no means and tools for treating persons afflicted of heart failure with preserved ejection fraction (HFPEF). The prior art therefore represents a problem.

SUMMARY OF THE INVENTION

The present invention provides a pharmaceutical composition for treatment of persons afflicted of chronic heart failure with preserved ejection fraction (HFPEF) and stiffening of the heart muscle, the composition comprising a therapeutically effective amount of a compound capable of specific binding to the relaxin receptor (RXFP1) present on fibroblasts, fibromyoblasts, endothelial cells, endocardial cells, and cardiomyocytes in the cardiac muscle to increase heart compliance and stroke volume and to lower the end-diastolic pressure of the left ventricle. The provided pharmaceutical composition can particularly be use and administered for treating the effects of a deficient phosphorylation of the cardiospecific titin, notably a hypophosphorylation of the cardiospecific titin N2B. The composition may comprise human relaxin molecules or a pharmaceutically acceptable derivative or precursor thereof in admixture with a pharmaceutically acceptable adjuvant, carrier, diluent or excipient suitable for subcutaneous or intravenous injection or oral application.

The pharmaceutical composition may be formulated as an emulsion (oil-in-water or water-in-oil) for delivery to the oral or gastrointestinal tract mucosa. The relaxin may be contained in a delivery vehicle selected from among a micelle, inverse micelle, liposome, cubosome and a mixture thereof. A preferred embodiment concerns a composition wherein a mucoadhesive protein is associated with the delivery vehicle via a chemical or physical bond so that the composition adsorbs to the mucosa or is retained on a mucosal surface for effecting systemic delivery of the relaxin.

Another embodiment of the present disclosure relates to a composition which is for subcutaneous infusion of human relaxin at a rate in the range of 10 µg/kg/day to 1000 µg/kg/day or as oral application producing plasma concentrations equivalent to those achieved with sc. infusions. The relaxin is preferably administered at an infusion rate in the range of 30 µg/kg/day to 100 µg/kg/day.

The disclosure further provides a pharmaceutical composition for treatment of a subject suffering from chronic diastolic heart failure and diagnosed of a phosphorylation deficit of the cardiospecific titin. The subject may be renally impaired, having creatinine clearance in the range of 30 to 75 ml/min/1.73 m2 estimated according to the MDRD formula. The subject afflicted of chronic diastolic heart failure may be further hypertensive and/or suffering from diabetes and/or oxidative stress and/or inflammation, i.e. typical concomitant diseases and chronic conditions which lead to a deficient phosphorylation of the cardiospecific titin. Another aspect of the disclosure concerns a method for increasing cardiac inflow by administering to a patient exhibiting pathologically diminished cardiac inflow a therapeutically effective amount of a compound capable of specific binding to a relaxin receptor in the myocardium and lowering the heart's end-diastolic pressures and increasing the heart's stroke volume.

The pharmaceutical composition for treatment of persons affected by a chronic diastolic heart failure with preserved ejection fraction (HFPEF) caused by altered chemo-mechanical characteristics of the heart muscle proteins, notably titin, and more precisely by a hypophosphorylation of titin, said composition comprises a therapeutically effective amount of a compound capable of specific binding to relaxin receptor (RXFP1) present on fibroblasts, fibromyoblasts, endothelial cells and cardiomyocytes in the cardiac muscle to thereby increase the heart's stroke volume at lower pressures.

The disclosure further provides as active relaxin agent or ingredient the receptor binding core structure (minimal active structure) of human relaxin, or a pharmaceutically acceptable derivative or precursor thereof, in admixture with a pharmaceutically acceptable adjuvant, carrier, diluent or excipient suitable for parenteral administration. In a further embodiment, the pharmaceutical composition may comprise as active ingredient or agent at least one selected from the group comprising human relaxin-1, human relaxin-2, human relaxin-3 as well as analogues or derivatives thereof. A most preferred embodiment contains synthetic relaxin molecules which are bioequivalent to human relaxin-2. The synthetic human relaxin-2 may be chemically synthesized.

As mentioned, the pharmaceutical composition may be for injection, preferably for intramuscular, subcutaneous or, most preferably, for intravenous injection and the dose for human relaxin-2 may be in the range of 1 µg/kg/day to 1000 µg/kg/day. A subcutaneous injection is preferred for obtaining a slow release of the relaxin peptide, preferably human relaxin-2. An administration delivered directly to the veins through an intravenous drip may preferably be in the range from 5 µg relaxin-2/kg/day to 100 µg/kg/day.

It is further contemplated to administer the relaxin agent in a formulation as also used for an oral or nasal delivery and administration of insulin. Such a galenic formulation may comprise a functionally active amount of a mucoadhesive protein, a relaxin compound as described and, optionally, additional agents for delivery; and a delivery vehicle associated with the agents. The composition may be formulated as an emulsion (oil-in-water or water-in-oil) and for delivery to the oral or gastrointestinal tract mucosa. The mucoadhesive protein may be from among immunoglobulins, albumins, mucin proteins and transferrins. The mucoadhesive protein may be associated with the delivery vehicle via a chemical or physical bond, so that the composition adsorbs to the mucosa or is retained on a mucosal surface for effecting systemic delivery of the agent. The delivery vehicle may be selected from among a micelle, inverse micelle, liposome, cubosome and a mixture thereof. Such kind of targeted emulsions and formulations have been described in detail for example in EP 1 768 647 B1, U.S. Pat. No. 8,414,914. Exemplary formulations for an oral administration of relaxins have been described. WO2003/047494A2, U.S. Pat. No. 5,444,041 and WO 02/094221A1 are related to emulsion/microemulsion compositions, WO96/37215 A1 is related to peptide water in oil emulsions, US2006/0210622A1 is related to surface modified particulate compositions, WO 03/030865 A1, U.S. Pat. No. 5,206,219A and US 2004/097410A1 are related to peptide compositions including e.g. surfactants and/or lipid components, US2006/0182771 A1 is related to self-emulsifying compositions and WO2008/145730A1, WO 2008/145728A1 and Ma Er-Li et al., Acta Pharmacologica Sinica, October 2006, Vol. 27 (10): 1382-1388, are related to microemulsions or emulsion pre-concentrates. SMEDDS compositions are known to improve the solubility and oral bioavailability of polypeptides such as cyclosporine, insulin and relaxin. However, the solubility and bioavailability of hydrophilic water soluble polypeptides such as human insulin or relaxin in SMEDDS and SMEDDS may not always be optimal.

The pharmaceutical composition is preferably administered to a subject afflicted by heart failure with preserved ejection fraction (HFPEF) and diagnosed of at least one symptom which brings about a differential change in titin domain phosphorylation. The relaxin-induced changes in titin-domain phosphorylation have been observed to fine-tune passive myocardial stiffness so that the diastolic function of the heart can be recovered.

The titin-domain phosphorylation affecting symptom may be at least one of the non-limiting group comprising diabetes, high blood pressure, ischemia, arteriosclerotic vascular diseases or any one of the group of diseases causing oxidative stress and/or an undersupply of the heart with oxygen and nutrients (e.g. smoking) and which result in an altered titin-domain phosphorylation in the failing myocardium. An altered phosphorylation of titin (hypophosphorylation of titin N2B isoform) in the failing myocardium can for example be detected by isolating titin N2B from serum, e.g. titin exon 49 fragment released from the failing myocardium, and by determining its phosphorylation by mass spectrometry.

The disclosed pharmaceutical composition may be administered to patients having at least one of the group comprising diabetes, atherosclerosis and/or high blood pressure and at high risk developing a heart failure with preserved ejection fraction (HFPEF) due to altered chemo-mechanical characteristics of the myocardium. In a most preferred embodiment, the pharmaceutical composition is administered to a subject afflicted of DHF or HFPEF who is also renally impaired. This is for example the case, when the subject has a creatinine clearance in the range of 30 to 75 ml/min/1.73 m2. When the subject afflicted of DF, DHF or HFPEF is further hypertensive, the disclosed active ingredient may be administered as described but preferably in a pharmaceutical composition further comprising an antihypertensive drug. The antihypertensive drug may be selected from the group of anti-hypertensive drugs comprising vasodilators, adrenergic blockers, centrally acting alpha-agonists, angiotensin-converting enzyme inhibitors, angiotensin II receptor blockers, calcium channel blockers and diuretics.

Another aspect relates to a method for increasing cardiac inflow by administering to a patient exhibiting pathologically diminished cardiac inflow of a therapeutically effective amount of a compound capable of specific binding to a relaxin receptor in the myocardium and increasing the heart's stroke volume when the patient further exhibits either a non-typical expression of titin N2B, e.g. a shift in the expression of the titin isoforms N2B and N2A, or a deficient or hypo-phosphorylation of the cardiac protein titin N2B or both. The present invention shall however not be construed to be limited to a specific misphosphorylation of titin but relates to the posttranslational modifications of titin in general. It should be pointed out that the primary physiological effect of relaxin in the treatment of heart failure with preserved ejection fraction is the relaxin-induced change of the chemo-mechanical properties of the myocardium and an increased phosphorylation of titin domains, which also increases cardiac compliance and distensibility, rather than any one of the relatively unspecific vasodilatory effects associated with relaxin. Consequently, the method in accordance with this aspect of the invention comprises methods for administration of the pharmaceutical composition as described in any of the claims to a subject suffering from DF, DHR or HFPEF which is the result of a chemo-mechanical failure of the heart muscle.

BRIEF DESCRIPTION OF THE DRAWINGS

The present invention is best understood when read in conjunction with the accompanying figures, which serve to illustrate the preferred embodiments. It is understood, however, that the invention is not limited to the specific embodiments disclosed in the figures.

DETAILED DESCRIPTION OF THE INVENTION

The present disclosure relates to the treatment of patients afflicted of heart failure with preserved ejection fraction (HFPEF) and diastolic heart failure (DHF). More precisely, a relevant subgroup of these patients suffers from a phosphorylation deficit of the myocardial protein titin, also known as connectin, which then leads on to a heart failure with preserved ejection fraction (HFPEF). Titin is a large structural protein, one of the largest known, and encoded in humans by the TTN gene (Labeit S et al., *A regular pattern of two types of 100-residue motif in the sequence of titin*. Nature (1990) 345: 273-6. doi:10.1038/345273a0. PMID 2129545.) With a length of about 27,000 to 33,000 amino acids (depending on the splice isoform), the titin comprises roughly 200 to 250 individually folded protein domains which unfold when the giant protein is stretched and refold when the tension is removed. Variations in the sequence of titin between different types of muscle (e.g., cardiac or skeletal) have been correlated with differences in the mechanical properties of these muscles. This distinguishes the present invention from a use of relaxin or serelaxin (RLX030) aiming at a hypertension therapy and vasodilation as described e.g. by Vitovec J et al in *Kardiol Rev* 2013; 15(2):113-117. Those therapeutic application have been designed for treatment of various types of acute heart failure as described herein in the background section of the invention.

With respect to the striated heart muscle, titin can be regarded working like a molecular spring which is not only important in the contraction of the striated muscle tissues, but also considered responsible for the passive elasticity of muscle. There is a cardiac specific isoform of titin. More precisely, myofilament stiffness is dependent on the expression levels of the cardiac titin isoforms, N2B and N2BA, and by the phosphorylation of the elastic titin domains N2-B unique sequence (N2-Bus) and PEVK. Phosphorylation of N2-Bus by cAMP-dependent protein kinase (PKA) or cGMP-dependent protein kinase (PKG) decreases titin stiffness, whereas phosphorylation of the PEVK domain by PKC increases it. Thus, hypo-phosphorylation of the N2-Bus and hyper-phosphorylation of the PEVK domain act complementary to elevate passive tension in failing human hearts (Müller E A et al in *Cardiovasc Res* (2013) doi:10.1093/cvr/cvt144; published online: Jun. 13, 2013).

The above belongs to the general technical context that the cardiac muscle cell (myocyte) contains bundles of myofibrils which in turn are made up of myofilaments comprising myosin and actin. The myofibrils consist of microanatomical units, termed sarcomeres, which represent the basic contractile units of the myocyte. The sarcomere is defined as the region of myofilament structures between two Z-lines. The distance between Z-lines (i.e., sarcomere length) ranges from about 1.6 to 2.2 µm in human hearts, whereas the myocyte is about 25 µm in diameter and about 100 µm in length. Chemical and physical interactions between the actin and myosin cause the sarcomere length to shorten, and the myocyte to contract. Thus, the contracting sliding filaments on the one hand produce muscle contraction and titin filaments are needed on the other hand for passive-force generation and transmission of stress. Titin stiffness however varies during heart development and disease through a shift in the expression ratio of the two main titin isoforms in cardiac sarcomeres, N2BA (compliant) and N2B (stiffer). The stiffer N2B titin isoform is inter alia triggered by thyroid hormone activating the phosphatidylinositol-3-kinase pathway. Conversely, low thyroid hormone (T3) promotes the compliant N2BA-titin. In addition, titin stiffness can be tuned down acutely by protein kinase (PK)A- or PKG-mediated phosphorylation of a cardiac-specific 1-band titin segment, the N2-B domain. Accordingly, beta-adrenergic agonists, nitric oxide, or natriuretic peptides diminish the stiffness of titin molecular springs. Thus, an elevated passive stiffness of a human heart is likely caused by a titin N2B phosphorylation deficit which may go along with a mechanical dysfunction of the myocardium and syndromes such as HFPEF and DHF (for review, see Krüger et al., J Mol Cell Cardiol. (2009) 46(4):490-8; Kellermayer et al, J Muscle Res & Cell Motility (2002) 23(5-6): 499-511).

The present inventors have found that the titin-N2Bus domain phosphorylation deficit may be offset by the administration of relaxin. Without being bound by any theory, it is assumed that relaxin binds to the RLXFP1 receptor which activates the NO-cGMP-protein kinase G and/or cAMP-protein kinase A pathways in myocardial cells (fibroblasts, fibromyoblasts, cardiomyocytes, endocardial cells, endothelial cells). The increased phosphorylation activity then increases the passive compliance of the striated heart muscle which leads to a lowering of the left ventricular end-diastolic pressure. The relaxin protein superfamily includes insulin, insulin-like growth factors I and II and insulin-like factors 3, 4, 5 and 6. Three distinct forms of relaxin have been identified in humans whereof relaxin-2 (H2) is the major stored form and the only form known to be secreted into the circulation. Relaxin is a heterodimeric peptide hormone of about 6 kDa wherein an A chain and a B chain are linked via disulphide bridges. The biological role of human relaxin-1 (H1) is not clear to date and relaxin-3 (H3) is found in the brain only acting as a neuropeptide (Bathgate et al., Physiological Reviews 2013).

The efforts to identify relaxin receptors have led to the discovery of the G protein-coupled receptors LGR-7 (now classified as RXFP1) as the cognate receptor for relaxin-2 and GPCR-135 (now classified as RXFP3) as the physiological relaxin-3 receptor. Human relaxin-2 also binds and activates the human glucocorticoid receptor (GR) (Dschietzig T et al in FASEB J 2004; 18:1536e8). Human relaxin-1 and -2 further bind to the receptors LGR8 (now classified as RXFP2) and GPCR142 (now classified as RXFP4). However, RXFP1 is the only widely expressed receptor which binds each of the human relaxins (H1, H2 and H3) with high affinity. Thus, it can be assumed that all human relaxins display similar biological activity with respect to their ability to stimulate cAMP activity and other RXFP1-related pathways in cells expressing the RXFP1 receptor (for review see Bathgate R A et al., Physiol. Rev 2013).

The intrinsic physiological function of relaxin in man is still unclear. Relaxin was originally identified by its activity as a pregnancy hormone (see Hisaw F L et al, Proc. Soc. Exp. Biol. Med. 1926; 23:661-663). Since then, relaxin has been shown to act as an endocrine and paracrine factor causing a widening of blood vessels (vasodilatation) in the kidney, mesocaecum, lung and peripheral vasculature and to increase blood flow and perfusion in these tissues (Dschietzig & Stangl in CMLS 2002; 59:1-13 (Review); Dschietzig T et al in Circ Res. 2003; 92:32-40). A number of unrelated activities have further been attributed such as a regulator of vasotonus, plasma osmolality, angiogenesis, collagen-turnover, renal and myocardial function, and central nervous processes (see Dschietzig T et al in Cell. Mol. Life Sci. 2003; 60:688-700; Dschietzig T et al. in Pharmacol Ther 2006; 112:38e56, Nistri S et al in Cardiovasc Hematol Agents Med Chem 2007; 5:101e8). Aberrant relaxin activity and/or expression have been implicated in diverse disorders and diseases such as high blood pressure, drinking, memory-related functions and addictive behaviors by binding the receptors in the brain and circumventricular organs as well as for cardiovascular diseases, renal diseases, fibrotic disorders (including cardiac fibrosis and fibrosis associated with airway remodeling), neurological disorders, immune diseases and endometrial and reproductive disorders.

Numerous clinical applications using relaxin as well as relaxin agonists and antagonists have therefore been suggested, particularly for treating diseases related to vasoconstriction (EP07008840), as a co-factor or replacement of insulin (EP1909809), to increase arterial compliance (EP05731443), for tumor suppression (EP07719531), as adjuvant in the differentiation of stem cells (EP04806868), for increasing fertility (EP03005488) or control of fetal growth (EP5780049, EP98932799), for modulating apoptosis, for treating neurodegenerative dysfunctions, for promoting angiogenesis as well as even for promoting hair growth and inhibition of cutaneous aging (EP0793505).

The treatment of the stiffened heart muscle however is a medical indication clearly independent from the regulation of the vasotonus or other renal and myocardial functions. The instant pharmaceutical composition comprises relaxin molecules, more preferably human relaxin-2, which bind the RXFP1 receptor present on fibroblasts, fibromyoblasts, endothelial cells, endocardial cells, and cardiomyocytes in the myocardium (i.e., the entire cardiac muscle consisting of different cell types). The experiments hereinafter indicate that patients suffering from a titin N2B phosphorylation deficit and a stiffened heart muscle can obtain thereby an increase of the heart's stroke volume at lower pressures. Until this date, there has been no therapy of a diastolic stiffened heart muscle which leads to an increased distensibility and compliance of the heart muscle without the undesirable circumstances of a dilated heart.

Figure 1:
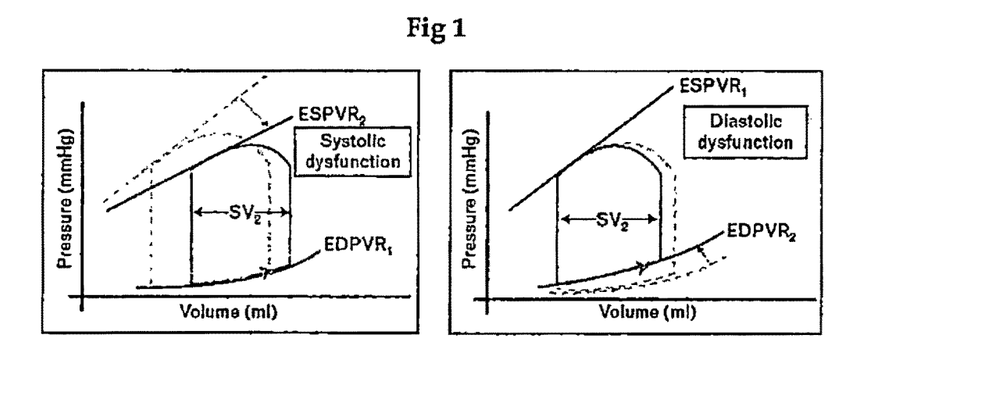
FIG. 1 are representative diagrams showing the pressure-volume relationship (ESPVR—end systolic pressure-volume relationship; EDPVR—end diastolic pressure-volume relationship) and stroke volumes (SV) in case of a systolic dysfunction (left) and a diastolic dysfunction (right)

More precisely, the heart muscle in diastolic heart failure (HFPEF) must be distinguished from a heart muscle in systolic heart failure (HFREF, heart failure with reduced ejection fraction). A dilated heart in HFREF has increased volume relative to the amount of diastolic pressure. In contrast, hearts in diastolic heart failure (HFPEF) show increased filling pressures already at normal or even slightly reduced volume (see also the diagrams in FIG. 1 depicting systolic [left] and diastolic heart failure [right]). Clinically, both different entities of heart failure, HFPEF and HFREF, may exhibit similar symptoms (edema, dyspnea, congestion, fatigue). The fact that in some patients suffering from systolic heart failure (HFREF), a diastolic dysfunction can also be detected does not weaken the fundamental differences: In systolic heart failure (HFREF), diastolic dysfunction might occur and is caused by and related to the leading systolic impairment. In diastolic heart failure (HFPEF), diastolic dysfunction in combination with a generally stiffened vascular bed prevails by far. These pathophysiological considerations correspond to the clinical and therapeutical situation: Contemporary medicine has at its disposal a remarkable variety of drugs (angiotensin-converting enzyme inhibitors, angiotensin receptor blockers, beta blockers, aldosterone antagonists, ivabradine) that lower mortality in systolic heart failure, but not one such drug exists for HFPEF despite absolutely comparable and even growing epidemiological relevance (Yancy et al. in JACC 2006;

Aurigemma G P et al in NEJM (2004) 351:1097-1105). Many drugs beneficial in HFREF have already failed in large clinical studies in diastolic heart failure: angiotensin-converting enzyme inhibitors and angiotensin receptor blockers failed in the PEP-CHF Trial (using perindopril), the CHARM-preserved Trial (candesartan), and in the I-PRESERVE Trial (irbesartan); beta blockers in the ELANDD Trial (nebivolol). Trials with aldosterone antagonists (RAAM-PEF testing eplerenone, ALDO-DHF evaluating spironolactone) have produced mixed results in recent phase-II trials and are far from having shown any mortality benefit.

Heart failure with preserved ejection fraction (HFPEF) is no rare disease. Up to half of all patients presenting clinical signs of heart failure suffer from diastolic heart failure and this particular entity is characterized by a normal ejection fraction (preserved systolic function) but increased left ventricular filling pressures and clinical signs of heart failure (Yancy C W et al. in J Am Coll Cardiol. (2006) 47(1):76-84). Mortality in this entity of heart failure is comparable to that in systolic heart failure (Owan et al. in NEJM 2006, 355: 251-259) so that a therapeutic treatment using a relaxin composition will achieve a favorable impact on the morbidity and mortality rates. Notably elderly patients (>70 yrs age) and patients with hypertension or diabetes may suffer from a titin phosphorylation deficit and a stiffened diastolic heart and they would benefit from a therapeutic treatment comprising an administration of relaxin. Thus, the need for a relaxin treatment is rising with the expectable demographic change in our society (Smith G L et al. in J Am Coll Cardiol (2003) 41:1510-8).

The disclosed composition preferably comprises a physiologically active amount of human relaxin molecules, most preferably a physiologically active amount of human relaxin-2 (H2) or a fusion protein with the active core of human relaxin which binds the RXFP1 receptor. U.S. Pat. Nos. 4,758,516 and 4,871,670 (Hudson et al) disclose the gene and protein sequences of human relaxin H1 and H2. Methods of synthesizing relaxin are described in U.S. Pat. No. 4,835,251 (Burnier et al), WO 2010/140060 (Barbs) and WO2013/17679 (Dschietzig T et al). Bioassays with synthetic relaxin H2 and analogues thereof have revealed a relaxin core structure bearing the biological activity (Dschietzig et al. in Pharmacol Ther. 2006; 112:38-56). A preferred embodiment therefore relates to a pharmaceutical composition comprising as active ingredient a compound having a relaxin core that binds to the RXFP1 receptor.

Recombinant H2 have already been tested in acute cardiovascular therapy and for treating neurodegenerative diseases (see U.S. Pat. No. 5,166,191 (Cronin et al) and Dschietzig T et al in. Journal of Cardiac Failure (2009) 15:182-190; Teerlink et al. in Lancet 2012, pii: 80140-6736 (12)61855-8; doi: 10.1016/S0140-6736(12)61855-8). The cardiovascular activity of relaxin-2 has further been evaluated in animal models (Perna A M et al. (2005) in FASE J, 19: 1525-1527; Bani, D. et al. in Am. J. Pathol. (1998) 152:1367-1376; Zhang J. et al. in Peptides (2005) 26: 1632-1639). These studies examine cardiac dysfunctions such as cardiomyopathy, diabetic cardiomyopathy, myocardial infarction or isoprenaline-induced cardiac toxicity for which established therapies are available, for example, an administration of angiotensin-converting enzyme inhibitors, angiotensin II receptor blockers, calcium channel blockers, diuretics, vasodilators, and beta blockers. A treatment of a stiffened diastolic heart muscle does not belong to these therapies. There have been also no successful clinical data concerning the treatment of HFPEF, cardiac fibrosis, valvular dysfunctions (abnormal thickening of the heart valves) and/or a fibrotic cardiac muscle may be concomitant, but unrelated medical indications. The latter is caused by over-activated fibroblasts and fibromyoblasts, not normally but excessively secreting collagen which leads to a loss of flexibility and distensibility of the heart muscle. A reduced structural support may however lead to a "dilated" or "remodeled" heart as also observed for drugs binding to the serotonin (5-hydroxytryptamin) receptor. While the administration of relaxin-2 reduces excessive collagen secretion and accumulation, it is pointed out that the activation of RXFP1 receptor on fibroblast and fibromyoblasts does not affect the basal collagen content in healthy tissues so that the administration of a RXFP1 agonist such as human relaxin-2 does not give rise to a dilated heart but is safe for therapeutic use in man.

Human relaxin-2 has also been tested as a peripheral and renal vasodilator, for increasing glomerular filtration rate and renal blood flow, and for augmenting endothelin type B receptor-mediated vasodilation and endothelin-1 clearance while it also stimulates the release of atrial natriuretic peptide. Others have shown that the administration of porcine relaxin induces favorable hemodynamic changes in intact rats, decreasing afterload and elevating the cardiac index without a significant drop of arterial pressure. Moreover, relaxin has been tested in human clinical trials as a therapeutic option for scleroderma patients and patients having chronic systolic heart failure (Seibold et al. in Annals of Internal Medicine 2000, 132:871-879; Dschietzig et al. in J of Cardiac Failure 2009, 15:182-190. The vasodilatory effects of relaxin have further been examined in studies with patients having acute decompensated heart failure (ADHF) and chronic systolic heart failure (CHF). These are again other medical indications for which other therapies are available and do not relate to the medical subgroup of chronic HFPEF due to altered chemo-mechanical characteristics of the proteins (titin) in the myocardium following oxidative stress or aging.

The present disclosure concerns the use of relaxin-2 for treating patients affected by a heart failure with preserved ejection fraction (HFPEF) and not in need of the vasodilatory activities of relaxin. This distinguishes the present invention from disclosures based on the vasodilatory effects of relaxin (WO 2013/017679). The latter activities result from a vascular activity occurring on endothelial cells and cells of the vascular smooth muscles such as found in the tunica media layer of large (aorta) and small arteries, arterioles, vein, as well as in lymphatic vessels, the urinary bladder, uterus (termed uterine smooth muscle), male and female reproductive tracts, gastrointestinal, tract, respiratory tract and around the glomeruli of the kidneys (these specialized smooth muscle-like cells are called mesangial cells).

While smooth muscle cells have basically the same structure and function in different organs, the cardiac muscle is a type of striated muscle and different to the skeletal and other smooth muscles. Thus, the present disclosure relates to an activity of human relaxin-2 mediated by the relaxin receptor (RXFP1) present on fibroblasts, fibromyoblasts, endothelial cells, endocardial cells, and cardiomyocytes in the myocardium. Such has not been suggested or described previously. In line with this, the N2B isoform of titin which is the therapeutic target of human relaxin-2 in the present disclosure is absolutely cardio-specific and not found in any other types of muscles (see for review Aronson and Krum, Pharmacol Therap 2012).

Chagas' heart disease is further said to represent a model of diastolic heart failure that spares systolic function (Marin-Neto et al. in Evidence-Based Cardiology, 3$^{rd}$ Ed., Yusuf S, Cairns J, Camm J et al (EDS), 2010, p 823ff). It is therefore contemplated using a relaxin-based composition as described for a treatment of Chagas myocarditis, say of patients seropositive for *Trypanosome cruzi* in order to preserve the distensibility of the heart muscle and to counter formation of a dilated heart. Without being bound by any theory it is contemplated that the *Trypanosoma* parasite causes a phosphorylation deficit and interferes with the structural properties of the titin isoforms.

Diagnosis of Diastolic Heart Failure (2013ICD-10-CM 150.3+4)

A patient is principally diagnosed having a diastolic dysfunction (HFPEF) when having the signs and symptoms of heart failure but a measured left ventricular ejection fraction close to normal or above 60%. Another diagnostic tool is an elevated BNP level in combination with a normal ejection fraction. Echocardiography may be used to diagnose diastolic dysfunction but no one single echocardiographic parameter can confirm a respective diagnosis. Multiple echocardiographic parameters have been proposed as sensitive and specific, including mitral inflow velocity patterns, pulmonary vein flow patterns, E:A reversal, tissue Doppler measurements (i.e., E/E' ratio), and M-mode echo measurements (i.e. of left atrial size). Algorithms have further been developed which combine multiple echocardiographic parameters.

There are four basic echocardiographic patterns of diastolic dysfunction, which are graded I to IV: The mildest form is called an "abnormal relaxation pattern", or grade I diastolic dysfunction. On the mitral inflow Doppler echocardiogram, there is reversal of the normal E/A ratio. This pattern may develop normally with age in some patients, and many grade 1 patients will not have any clinical signs or symptoms of heart failure. Grade II diastolic dysfunction is called "pseudo normal filling dynamics". This is considered moderate diastolic dysfunction and is associated with elevated left atrial filling pressures. These patients more commonly have symptoms of heart failure, and many have left atrial enlargement due to the elevated pressures in the left heart. Grade III and IV diastolic dysfunction are called "restrictive filling dynamics". These are both severe forms of diastolic dysfunction, and patients tend to have advanced heart failure symptoms: Class III diastolic dysfunction patients will demonstrate reversal of their diastolic abnormalities on echocardiogram when they perform the Valsalva maneuver. This is referred to as "reversible restrictive diastolic dysfunction". Class IV diastolic dysfunction patients will not demonstrate reversibility of their echocardiogram abnormalities, and are therefore said to suffer from "fixed restrictive diastolic dysfunction". The presence of either class III or IV diastolic dysfunction is associated with a significantly bad prognosis. These patients will have left atrial enlargement. Imaged volumetric definition of systolic heart performance is commonly accepted as ejection fraction. Volumetric definition of the heart in systole was first described by Adolph Fick as cardiac output. Fick may be readily and inexpensively inverted to cardiac input and injection fraction to mathematically describe a diastolic dysfunction. Decline of injection fraction paired with decline of the E/A ratio and an increase of the E/E' ratio seems a stronger argument in support of a mathematical definition of diastolic heart failure. Regardless of any systolic dysfunction and severity, a diastolic dysfunction can be beneficially treated using a relaxin-based composition when the decreased compliance and distensibility of the heart muscle is caused by a phosphorylation deficit of the relevant titin isoforms.

Diagnosis of an Altered Phosphorylation Pattern of Titin (Titin N2B Isoform).

The titin exon 49 isoform (Genbank AJ277892—Freiburg A et al., Circulation Research, 86, 1114-1121) is for example released into the circulation in case of a damaged heart. The amino acid sequence of titin exon 49 is cardiospecific since no such isoform occurs in other skeletal or smooth muscles. The cardiac specific titin exon 49 sequence comprises 928 amino acids (exon 49) and can be detected in serum and isolated therefrom. The detection limit for serum titin N2B protein is about 10 pg/mL and there are monoclonal antibodies available which can be used as capture antibodies for immunological purification of titin N2B from serum (DE 10 2012 017 566.3—Labeit D et al.). The purified titin N2B may then be examined for its phosphorylation using electrophoresis (Borbely A et al. in Circ. Res 2009, 104(6): 780-6) or preferably mass spectrometry (Kötter S et al in *Cardiovasc Res* 2013, doi: 10.1093/cvr/cvt/44).

Other indirect markers for a titin phosphorylation deficit may be increased levels of plasma or serum nitrotyrosine and interleukin-6, both markers for oxidative stress. Patients with diastolic heart failure also have significantly increased plasma levels of tumor necrosis factor alpha and interleukin 6 and 8 compared with control subjects. Nitrotyrosine expression, a measure of nitrosative/oxidative stress, correlates in particular with myocardial protein kinase G activity (PKG) and downstream with the titin phosphorylation activity in cardiomyocytes. It has already previously been speculated that the correction of the myocardial protein kinase G activity could be a target for specific HFPEF treatment but no pharmaceutical composition to this effect had been proposed. In this context, human relaxin-2 is unique because it directly stimulates the cGMP-PKG path by increasing nitric oxide, but also indirectly protects the bioavailability of nitric oxide and the functional integrity of soluble guanylate cyclase (i.e., the enzyme producing cGMP upon stimulation by nitric oxide) by its anti-oxidative and anti-inflammatory effects (Dschietzig T et al., Cardiovasc Res 2012).

EXAMPLES

Example 1

Synthetic Human Relaxin-2 and Bioequivalency (Prior Art)

The human relaxin-2 was prepared as disclosed in WO 2013/17679 (Dschietzig T et al) using a modification of the Merrifield method (Merrifield R B. Solid phase synthesis (Nobel Lecture) Angew. Chem Int. Ed. 1985; 24: 799-810). In essence, the process for preparing human relaxin-2 comprised the solid state synthesis of the following amino acid sequences:

```
SEQ ID NO: 1-A chain
pGlu-Leu-Tyr-Ser-Ala-Leu-Ala-Asn-Lys-Cys-Cys-His-
Val-Gly-Cys-Thr-Lys-Arg-Ser-Leu-Ala-Arg-Phe-Cys SEQ ID NO: 2-B chain:
Asp-Ser-Trp-Met-Glu-Glu-Val-Ile-Lys-Leu-Cys-Gly-
Arg-Gru-Leu-Val-Arg-Ala-Gln-Ile-Ala-Ile-Cys-Gly-
Met-Ser-Thr-Trp-Ser
```

For an intrachain bridge of the A chain (Cys-10 with Cys-15) and the combination the A and B chain (Cys-11 of A with Cys 11 of B and Cys-24 of A with Cys-23 of B) the A and B chains were first synthesized using trityl-protected cysteines (L-Cys(Trt)-OH). The individual chains A and B were purified after solid state synthesis by chromatography followed by simultaneous folding and combination of the individual chains A and B in an ammonium hydrogen carbonate buffer at pH 7.9 to 8.4; and subsequent purification of the relaxin-2 formed.

The prepared peptide hormone was structurally identical and bioequivalent to human relaxin-2 and recombinant human relaxin-2. Experiments were conducted in HEK293T cells over-expressing the RXFP1 receptor, an established cell line for basic receptor pharmacology, and in THP-1 cells, a human macrophage cell line with endogenous RXFP1 expression. The binding properties were determined using respective cells plated on 96-well IsoPlate™ microplates (PerkinElmer) with white walls and clear bottoms precoated with poly-L-lysine. The comparative binding was determined with europium-labeled human relaxin-2 as tracer and increasing concentrations of synthetic human relaxin-2 (two different lots). The unspecific binding was determined in the presence of an excess (500 nM) of unlabeled human relaxin-2. Each concentration point was determined in triplicate. The peptides were tested in at least three independent assays to confirm activity. Curves were fitted using a one site binding model in GraphPad Prism 4.0 (GraphPad Software, San Diego, Calif., USA). The inhibition constants (KI) as a measure of peptide activity were determined from the $IC_{50}$ values using the Cheng-Prusoff equation.

HEK-293T cells stably expressing RXFP1 and a pCRE-β-galactosidase reporter plasmid were further employed to determine the ability of synthetic human relaxin-2 (shRlx) to activate RXFP1-related signaling (Halls M L et al. in Ann NY Acad Sci. 2009; 1160:108-11). Stimulation of the RXFP1 receptor results in the activation of adenylate cyclase and therefore in an increase in cAMP. Cells were incubated for 6 hours with increasing concentrations of synthetic human relaxin-2 of two different lots and relaxins from other sources as indicated. Each concentration point was performed in triplicate and peptides were tested in at least three independent experiments. Data were analyzed with GraphPad Prism 4.0 (GraphPad Software, San Diego, Calif., USA), and a nonlinear regression sigmoidal dose-response (variable slope) model was used to plot curves and calculate $pEC_{50}$ values.

Figure 3:
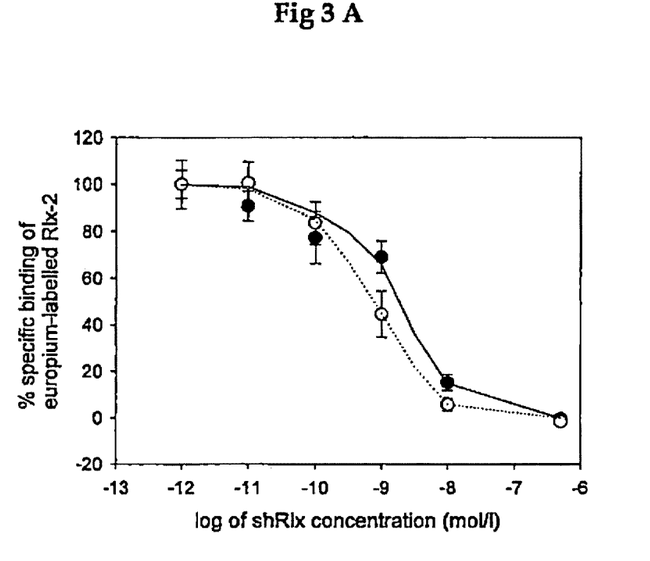
FIG. 3A is a plot of a completion binding experiment showing the bioequivalency of europium-labeled human relaxin-2 (cf: Shabanpoor F et al., Biochem Biophys Res. Commun. (2012) 420(2): 253-6) using human embryonic kidney (HEK)-293T cells stably transfected with RXFP1 receptor.
FIG. 3B is a plot showing the relationship between cAMP activity (cAMP reporter gene assay) in cells stably transfected with RXFP1 receptor and synthetic human relaxin-2 (cf. Yen Y et al. in *Biochemistry*, 2008, 47(26): 6953-6968)

The synthetic human relaxin 2 peptide bound equally as recombinant human relaxin-2 to human relaxin receptor RXFP1 (relaxin family peptide receptor 1); see Table 1 and FIG. 3A. Signal transduction was also similar as shown by the cAMP assays developed for human relaxin-2; see FIG. 3B. On human THP-1 cells, synthetic and recombinant human relaxin-2 showed equivalent bioactivities; see Table 1 below for details

TABLE 1

Testing of different lots of hRLX-2 for RXFP1 binding and cAMP generation

| Peptide | RXFP1 binding | | cAMP response |
|---|---|---|---|
| | pKi | pIC50 | pEC50 |
| HEK293T cells overexpressing RXFP1 | | | |
| shRlx, lot 01 | 8.9 ± 0.12 (3) | 8.8 ± 0.11 (3) | 10.1 ± 0.12 (3) |
| shRlx, lot 02 | 9.3 ± 0.15 (3) | 9.2 ± 0.15 (3) | 10.4 ± 0.04 (3) |
| -Asp-shRlx | | | 10.2 ± 0.03 (4) |
| rhRlx, Bathgate 2006 | 10.2 ± 0.26 (3) | | 10.6 ± 0.04 (4) |
| rhRlx, Hossain 2008 | 9.2 ± 0.16 (3) | | 10.4 ± 0.04 (4) |
| rhRlx, Yan 2008 | | 9.4 ± 0.11 (10) | 10.6 ± 0.05 (16) |
| rhRlx, Halls 2009 | | 9.6 ± 0.17 (4) | 9.4 ± 0.22 (7) |
| rhRlx, Hossain 2011 | | 9.0 ± 0.06 (8) | 10.3 ± 0.04 (5) |
| rhRlx, Scott 2012 | | 8.8 ± 0.05 (3) | 10.7 ± 0.04 (3) |
| rhRlx, Chan 2012 | 9.7 ± 0.07 (5) | | 10.7 ± 0.16 (5) |
| THP-1 cells | | | |
| shRlx, lot 01 | | | 9.1 ± 0.19 (3) |
| shRlx, lot 02 | | | 9.2 ± 0.32 (3) |
| rhRlx, Halls 2009 | | | 9.3 ± 0.12 (6) |

Table 1: Mean ± standard deviation (number of experiments in parentheses) of pKi and pIC50 values reflecting RXFP1 binding and of pEC50 reflecting cAMP generation.
pKi: negative decadic logarithm of the inhibition constant Ki;
pIC50: negative decadic logarithm of the 50% inhibitory concentration;
pEC50: negative decadic logarithm of the half-maximum concentration;
shRlx: synthetic human relaxin-2 of example 1;
-Asp-shRlx is the single aa degradation product of synthetic human relaxin-2;
rhRlx: human relaxin-2 prepared by recombinant cells.

Moreover, in an established cell model of myocardial hypertrophy (Dschietzig T et al. in Pharmacol. Ther. 2006; 112: 38-56) synthetic human relaxin-2 proved as potent as recombinant human relaxin-2. In our model, synthetic human relaxin-2 inhibited the differentiation of cardiac fibroblasts into myofibroblasts and the secretion of growth factors by these cells. The synthetic human relaxin-2 had excellent stability. A biologically fully active by-product without the N-terminal aspartate of the B chain was observed after 80 days at 37 degrees Celsius.

Example 2

Safety and Dose Response (First Medical Indication—Prior Art)

Human relaxin is physiologically up-regulated and plays a compensatory role in human heart failure like B-type natriuretic peptide. For determining the safety and dose response to human relaxin (recombinantly produced human relaxin-2, rhRLX) in stable patients with heart failure sixteen patients were treated with intravenous human relaxin-2 in three sequential dose cohorts and monitored hemodynamically during the 24-h infusion and post-infusion periods.

The safety demonstrated in group A (treatment for 8 h each with dosages equivalent to 10, 30, and 100 μg human relaxin-2/kg/day) allowed escalation to group B (240, 480, and 960 μg/kg/day), and the highest safe dose, 960 μg/kg/day, was selected for a 24-h dosing in group C.

The human relaxin-2 showed no relevant adverse effects and produced hemodynamic effects consistent with systemic vasodilation, i.e., trends toward increases in the cardiac index and decreases in pulmonary wedge pressure, without inducing hypotension. Thus, the demonstrated hemodynamic effects of human relaxin-2 represent a first therapeutic use of intravenously administered human relaxin-2 in human heart failure, notably congestive heart failure (Dschietzig et al. in FASEB Journal 2001, 15:2187-2195; BfArM approved study, "*A Pilot Safety and Dose-Finding Trial of Intravenous Recombinant Human Relaxin (rhRlx) in Compensated Congestive Heart Failure*", EudractCT 2005-001674-27, Protocol No RLX-CHF.001). An intravenous administration of human relaxin-2 has also been favorably tested in clinical phase III for its hemodynamic effects in cases of acute heart failure (Teerlink et al., *Relaxin for the treatment of patients with acute heart failure (Pre-RELAX-AHF): a multi-centre, randomised, placebo-controlled, parallel-group, dose-finding phase IIb study*. Lancet 2009, 373:1429-1439; (6) Ponikowski et al., *Design of the Relaxin in acute heart failure study*. American Heart Journal 2012, 163:149-155). Consequently, there are sufficient data that human relaxin-2 can be safely administered for treatment of heart failures.

Example 3

Treatment of Diastolic Dysfunction by Subcutaneous Infusion of Relaxin

Relaxin is known playing a role in the transformation of fibrocytes to fibromyoblasts, the initial step for the development of tissue fibrosis, and to modulate and attenuate the stimulated secretion of matrix proteins by fibromyoblasts (Samuel et al. in Endocrinology 2004, 145:4125-4133). Thus, relaxin may also be used to mitigate myocardial hypertrophy (Dschietzig et al in Annals of the NY Acad, of Science 2005, 1041:441-3; Moore et al. in Endocrinol. 2007, 148:1582-1589; Samuel et al., in Endocrinology 2008, 149: 3286-3293; Lekgabe et al. in Hypertension 2005, 46:412-418; Xioa-Jun Du et al in Cardiovascular Res 2003, 57:395-404). These disclosures however relate to processes due to a fibrotic or hypertrophic stiffening of the heart muscle, unrelated to the chemo-mechanical stiffening of the muscle proteins.

The present inventors have therefore used an animal model for testing the treatment for DHF and of a stiffened heart muscle having insufficient relaxation and distensibility. The table below summarizes data obtained in mice with a type of diastolic heart failure as compared with controls. The subcutaneous infusion of isolated porcine relaxin over 12 weeks in mice (50 μg porcine relaxin/kg/d) decreased end-diastolic pressure and, consequently, improved E/A ratio, a functional parameter indicating the quality of ventricular filling. The subcutaneous infusion of relaxin was obtained by implanting in the neck portion of the mice a membrane capsule releasing continuously porcine relaxin. The results have been summarized in Table 2 below:

TABLE 2

Treatment of diastolic dysfunction by subcutaneous infusion of relaxin

| | Controls | | | | Diastolic Dysfunction | | | |
|---|---|---|---|---|---|---|---|---|
| | Baseline before Placebo (n = 15) | Placebo 12 weeks (n = 15) | Baseline before Relaxin (n = 15) | Relaxin 12 weeks (n = 15) | Baseline before Placebo (n = 15) | Placebo 12 weeks (n = 15) | Baseline before Relaxin (n = 15) | Relaxin 12 weeks (n = 15) |
| LVSP | Nd | 121 ± 13 | Nd | 109 ± 10 | Nd | 112 ± 13 | nd | 111 ± 12 |
| LVEDP | Nd | 5.0 ± 0.4 | Nd | 5.2 ± 0.5 | Nd | 10.7 ± 1.0* | Nd | 7.0 ± 0.6*§ |
| E/A ratio | 2.5 ± 0.2 | 2.3 ± 0.3 | 2.6 ± 0.2 | 2.4 ± 0.2 | 1.5 ± 0.1* | 1.4 ± 0.2* | 1.6 ± 0.1* | 2.0 ± 0.2# |

Data, given as mean ± SEM, were obtained in mice.
LVSP (mmHg): left ventricular systolic pressure as measured by invasive micromanometry;
LVEDP (mmHg): left ventricular end-diastolic pressure as measured by invasive micromanometry;
E/A ratio: ratio of echocardiographically determined mitral flow velocities.
*$P < 0.05$ compared with controls;
$P < 0.05$ compared with baseline (Friedman ANOVA on ranks);
§$P < 0.05$ compared with placebo;
nd: not determined - as the mice had to be sacrificed after catheterization, no baseline catheter measurements could be made prior to administration of placebo or relaxin.

The data show that the subcutaneous infusion of porcine relaxin had a beneficial effect on the heart function of diastolic mice only whereas no pharmaceutical effects were noted in the controls. Thus, relaxin proved effective when the performance of the heart was already endangered by stiffening actions. In the controls the measured E/A ratio was not affected in any way (E/A=2.5 or 2.6±0.2). However, in case of a diastolic dysfunction the reduced E/A ratio dramatically shifted back to the normal range showing that the administration of relaxin has greatly improved the diastolic functions of the mice hearts. Thus, the data support that the treated hearts had improved distensibility and relaxation. Notwithstanding, there was a need to understand the effects of relaxin and the underlying mechanism to this observation.

Example 4

Myocardial Production of Endogenous Human Relaxin-2

Figure 2:
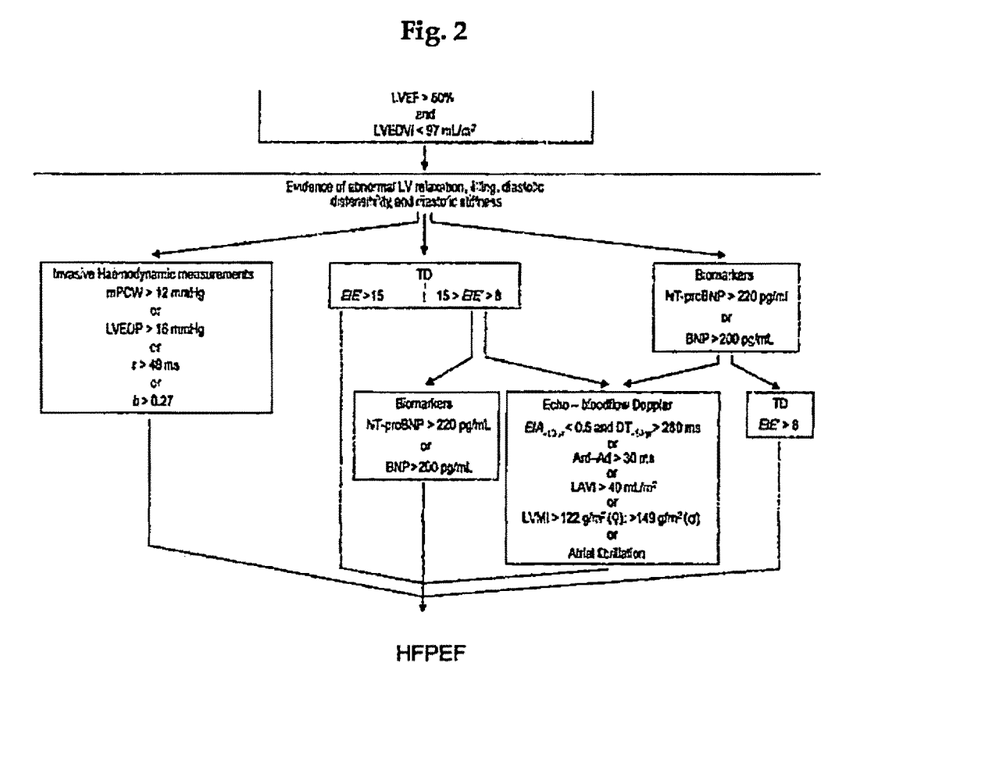
FIG. 2 is a diagnostic flow chart in accordance with Paulus W J et al., *How to diagnose diastolic heart failure: a consensus statement by the Heart Failure and Echocardiography Associations of the European Society of Cardiology*. European Heart Journal (2007) 28(20): 2539-2550.

Among patients undergoing elective catheterization for ablation of atrial fibrillation, we recruited 20 control patients (5 postmenopausal women, 15 men) without systolic or diastolic heart failure and 30 patients (10 postmenopausal women, 20 men) suffering from diastolic heart failure (DHF) as diagnosed using the diagnostic algorithm according to Paulus et al., see FIG. 2.

Blood for determination of relaxin-2 by ELISA was drawn immediately before the ablation procedure from antecubital vein, aorta/left ventricle, and coronary sinus. The concentration difference between aorta/left ventricle and coronary sinus was termed the coronary gradient. A positive gradient (coronary sinus level >aortic/left ventricular level) was considered a measure of myocardial relaxin production, a negative one was indicative of myocardial consumption of circulating relaxin.

Figure 4:
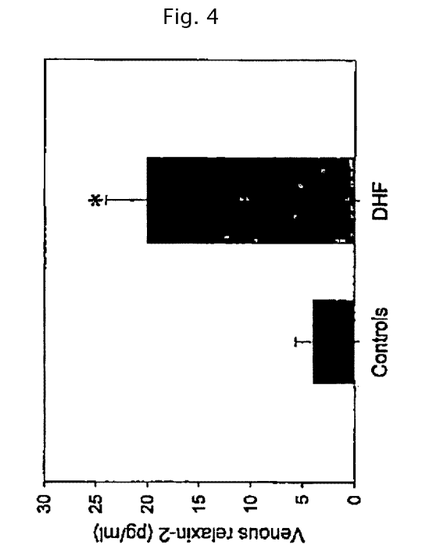
FIG. 4 is a bar graph showing the endogenous venous relaxin-2 concentration in patients afflicted of DHF and controls (P<0.05 versus controls; Mann-Whitney U test on ranks)
Figure 5:
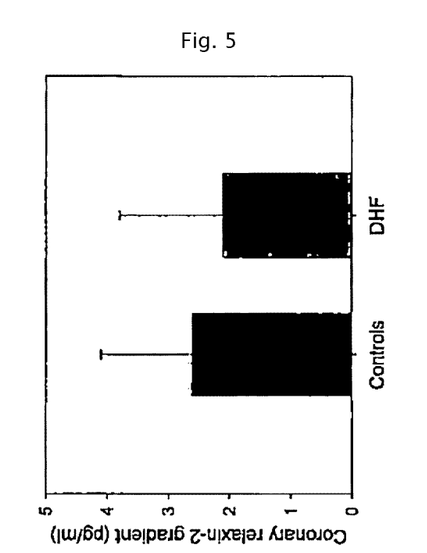
FIG. 5 is a bar graph showing the coronary concentration gradient of endogenous relaxin-2 in patients afflicted of DHF and controls (analyzed with a two-factorial ANOVA (factors: group, repeated measures; P>0.05, no significant difference)
Figure 6:
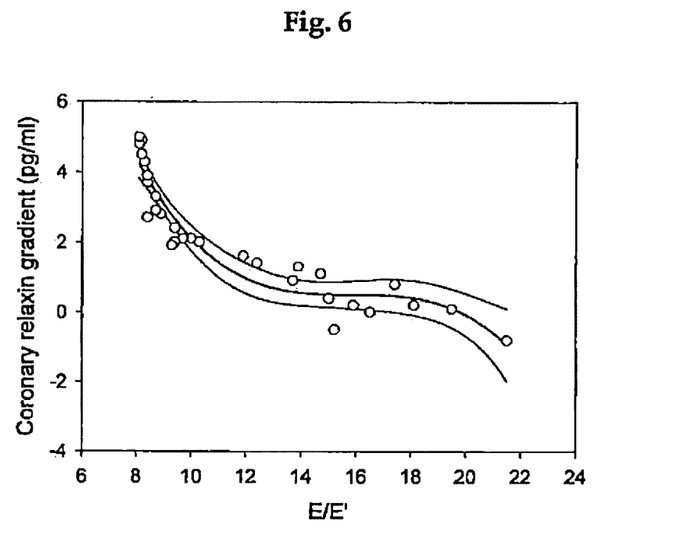
FIG. 6 is a plot showing the coronary concentration gradient of endogenous relaxin-2 relative to the diastolic dysfunction in patients as determined by the echocardiographic marker E/E' wherein E denotes early mitral valve flow velocity and E' denotes early myocardial relaxation velocity as measured by tissue Doppler.

Circulating (venous) relaxin-2 was significantly increased in patients with diastolic heart failure (DHF) as compared with controls; see FIG. 4 ($P<0.05$ versus controls; Mann-Whitney U test on ranks). Regarding the coronary gradient of relaxin-2 we did not find any significant difference between controls and DHF patients; see FIG. 5 (Analyzed with a two-factorial ANOVA (factors: group, repeated measures); P>0.05, no significant difference). However, when we analyzed the relation between coronary relaxin-2 gradients and an echocardiographic measure of diastolic dysfunction (E/E', see below) in DHF patients, we found a highly significant non-linear inverse correlation. In other words, the hearts of DHF patients with high relaxin gradients (reflecting high myocardial production) perform better in diastole than those of DHF patients with low or even negative gradients. The results of this analysis are shown in FIG. 6: Individual coronary gradients of relaxin-2 in DHF patients in dependence of diastolic function as assessed by E/E'. E/E' is the most established echocardiographic marker of diastolic dysfunction which is used to classify and diagnose DHF (see Paulus et al., Eur Heart J 2007; FIG. 2). E denotes early mitral valve flow velocity, E' denotes early myocardial relaxation velocity as measured by tissue Doppler; E/E' is the dimensionless ratio thereof. Cubic regression with 95% confidence intervals; Pearson correlation coefficient r=0.95. in controls, no such correlation was found.

These findings give rise to the conclusion that the individual lack of myocardial relaxin-2 up-regulation worsens the individual degree of diastolic dysfunction. Vice versa, therapeutic relaxin administration is expected to improve DHF significantly. Most importantly, it should be noted that human relaxin-2 affects the fibroblasts and myofibroblast of the heart and that these beneficial effects have no hemodynamic origin, say do not come from the vasodilatory effects of human relaxin-2.

Example 5

Correlation between Inflammation/Oxidative Stress and Left Ventricular End Diastolic Pressure and Altered Titin N2B Hypophosphorylation by the Administration of Relaxin-2

Hearts from male 5-month old control and spontaneously hypertensive (SHR) rats as well as from 12-week old Zucker Lean (Lean) and Zucker Diabetic Rats (ZDF) were excised and mounted as Langendorff preparations (n=16 each). Similarly, hearts were also taken from wild-type (WT) and heterozygous β2-adrenoreceptor transgenic (TG) mice generated from heterozygous (C57B1k6J×SJL) parents (n=10 each). The β2-adrenoreceptor transgenic (TG) mouse is a model with prevailingly fibrosis-related diastolic dysfunction.

During prior exsanguination of the animals, blood had been taken for the determination of plasma nitrotyrosine and interleukin-6 (IL-6). The left ventricular end-diastolic pressure (LVEDP) at maximum left ventricular systolic pressure development (active LVP) was determined. Thereafter, all hearts were treated with 5 nmol/L synthetic human relaxin-2 or placebo for 30 min (n=8 for each subgroup). Eventually, the total and phosphorylated N2BA and N2B titin isoforms were detected and quantified in homogenates of the free left ventricular wall.

Baseline: At maximum active LVP, SHR hearts showed significantly elevated LVEDP as compared with control hearts: SHR, 14±2 mm Hg; control, 5±1 mm Hg. Likewise, ZDF hearts had higher LVEDP than Lean hearts: ZDF, 12±2 mm Hg; Lean, 6±1 mm Hg. P<0.01; and TG mice had significantly higher LVEDP than WT mice: TG, 12.3±2 mm Hg; WT, 4.9±1.1 mm Hg (Kruskal-Wallis ANOVA on ranks followed by Mann-Whitney U-test).

Figure 7:
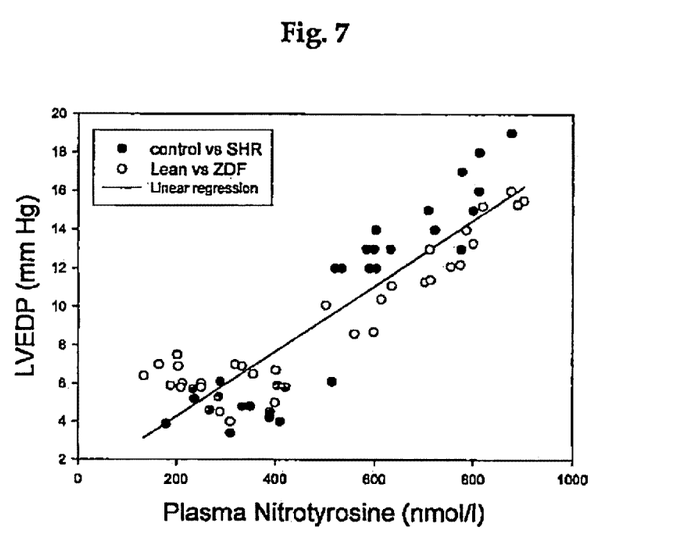
FIG. 7 is a plot showing the correlation and linear regression between the left-ventricular end-diastolic pressure LVEDP (mmHg) and a circulation marker for oxidative stress, plasma nitrotyrosine (nmol/L), in two independent animal models of DHF (SH and ZDF rats—SH: spontaneously hypertensive; ZDF: Zucker Diabetic Fatty); and appropriate controls (Lean: Zucker lean) and controls.

Plasma levels of nitrotyrosine and IL-6 correlated with baseline LVEDP, both in the control-SHR and in the Lean-ZDF cohorts of rats. FIG. 7 shows this correlation in the rat groups for nitrotyrosine and LVEDP; Pearson's correlation coefficient was r=0.89 over all rat groups (P<0.01). Likewise, a positive correlation between plasma IL-6 and LVEDP was found, with r=0.91 over all rat groups (P<0.01). No such correlation was found in the WT and TG mice.

Effect of Relaxin-2 on LVEDP (Treatment)

Figure 8:
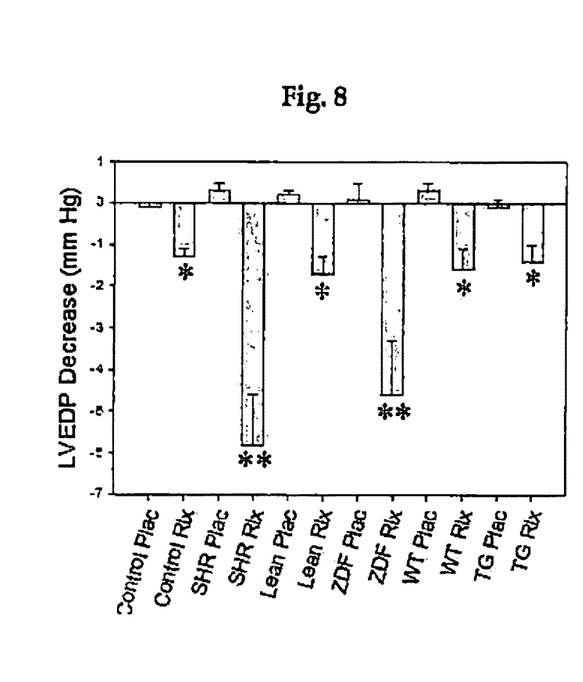
FIG. 8 is a bar chart showing the decrease of the left ventricular end-diastolic pressure by an administration of synthetic relaxin-2 (5 nmol/L) for 30 minutes in the animal models of FIG. 7 (Plac: placebo; Rlx: relaxin-2; SHR: spontaneously hypertensive rat; ZDF: zucker diabetic fatty rat; Lean: zucker lean rat; Control: control rat for SHR)

As compared with placebo, 5 nmol/L of synthetic human relaxin-2 administered for 30 min markedly decreased LVEDP in the SHR and ZDF hearts whereas smaller changes were seen in control and Lean hearts. In WT and TG mice, synthetic human relaxin-2 evoked small, but significant LEVEDP decreases which, in contrast to the data obtained in the two rat models, did not differ between controls (WT) and diseased animals (TG). The bar chart of FIG. 8 summarizes the resulting physiological effect on the heart in terms of the mean decreases in LVEDP in the different groups (* indicates P<0.05 vs placebo; **, P<0.01, Kruskal-Wallis ANOVA on ranks followed by Mann-Whitney U-test). The administration of relaxin-2 had clearly a substantive beneficial effect on hearts of ZDF and SH rats which suffered from oxidative stress and altered mechanical properties of the cardiac muscle.

Effect of Relaxin on Titin Phosphorylation

Figure 9:
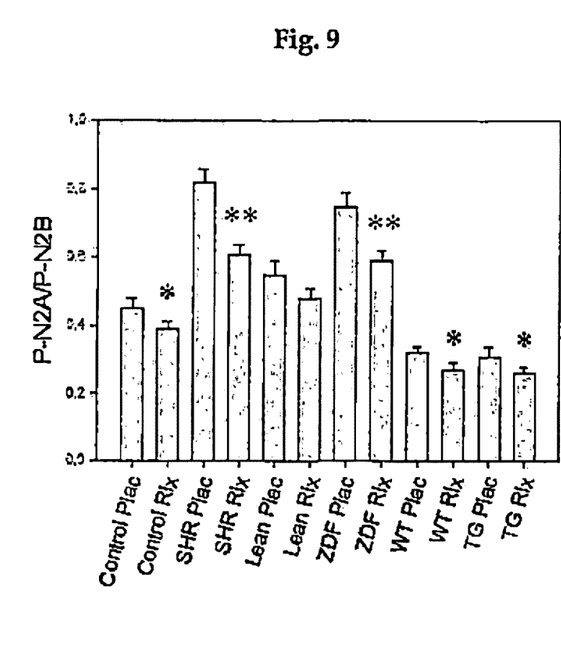
FIG. 9 is a bar chart showing the shift in titin phosphorylation from N2B to N2BA isoform (expressed as phosphorylated titin P-N2BA/P-N2B isoform ratio) by synthetic relaxin-2 (5 nmol/L) for 30 minutes in the animal models of FIG. 7 (Plac: placebo; Rlx: relaxin-2; SHR: spontaneously hypertensive rat; ZDF: zucker diabetic fatty rat; Lean: zucker lean rat; Control: control rat for SHR).

In contrast to placebo, 5 nmol/L of synthetic human relaxin-2 administered for 30 min significantly reversed the relative hypophosphorylation of the stiff titin N2B isoform (which is expressed here as ratio P-N2BA/P-N2B) found in SHR and ZDF hearts. In contrast, the relative phosphorylation status of N2B titin was not changed in TG as compared with WT mice (comparison of the WT and TG placebo groups), and the relaxin effect did not differ between controls (WT) and diseased animals (TG). FIG. 9 summarizes the mean P-N2BA/P-N2B ratios in the different groups (* indicates P<0.05 vs placebo; **, P<0.01, Kruskal-Wallis ANOVA on ranks followed by Mann-Whitney U-test).

In all rat groups examined, but not in mice, we found a significant correlation between the P-N2BA/P-N2B ratio of the placebo-treated hearts of all groups and baseline LVEDP (Pearson's r=0.75 over all groups [P<0.01]) Thus, the increased baseline LVEDP found in hearts with DHF correlates with the relative N2B phosphorylation deficit (P-N2BA/P-N2B ratio) and the baseline LVEDP can be lowered by the administration of relaxin-2 which decreases the P-N2BA/P-N2B ratio by increasing the N2B phosphorylation.

Discussion of Results

The giant protein titin poses the major determinant of myocardial diastolic stiffness (Borbely et al., Circ Res 2009; 104:780-786; Paulus and Tschoepe, JACC 2013; 62:263-271). An increased myocardial diastolic stiffness with concomitantly increased left ventricular filling pressure (LVEDP) is further a most clear diagnostic sign for the presence of HFPEF (diastolic heart failure, diastolic dysfunction) and that HFPEF (heart failure with preserved ejection fraction, HFPEF) can not only be related to a hypophosphorylation of the stiff N2B titin isoform but that an impaired titin phosphorylation is attributable to increased oxidative stress which compromises the bioavailability of nitric oxide. It has previously been shown that the latter diminishes cGMP-protein kinase G signaling and N2B phosphorylation (Heerebeek et al., Circulation 2012; 126: 830-839). The present inventors have further presented evidence that synthetic human relaxin-2 is capable of increasing the cAMP activity in RXFP1 cells, which can offset a phosphorylation deficit of the titin isoforms, which also leads to an improvement (lowering) of pathologically elevated LVEDP in two independent animal models of diastolic dysfunction, SHR and ZDF. It was further demonstrated for the first time that the decreasing effect of relaxin on LVEDP is accompanied by elevated N2B phosphorylation. In our models, the circulating markers of oxidative stress and/or inflammation, nitrotyrosine and interleukin-6, correlated with the degree of diastolic dysfunction (LVEDP increase) and with the degree of relative N2B hypophosphorylation. On the other hand, in the model with prevailingly fibrosis-related diastolic dysfunction, the β2-adrenoreceptor transgenic mouse, there is not phosphorylation deficit of N2B titin which could be treated by the administration of relaxin. Thus, the effects of synthetic relaxin-2 did not differ between controls and diseased animals. Accordingly, synthetic human relaxin-2 is a candidate drug to treat patients suffering from DHF who demonstrate high plasma levels of oxidative/inflammatory markers indicative of increased diastolic myocardial stiffness owing to titin N2B hypophosphorylation.

Example 7

Testing of DHF Patients (Clinical Phase II) with Synthetic Human Relaxin-2

The official approval of the clinical phase II is being obtained for patients diagnosed of diastolic heart failure as described by Paulus et al., see diagram of FIG. 2 The criteria for inclusion in the DHF study are a) hospitalization for dyspnea within the last six months; b) a stable medication for at least four weeks prior treatment; c) a left ventricular ejection fraction (LVEF)—preserved ejection fraction of at least 50%; d) an established diagnosis of HFPEF according to Paulus et al. (see diagram with diagnostic flow chart, FIG. 2). Excluded from the study are patients having any relevant systolic dysfunction, or an acute coronary syndrome within the last 4 weeks, or an acute myocardial infarction or a heart surgery within the last six months, or hypotension (a systolic blood pressure of less than 100 Hg), or life-threatening tachycardia or bradycardia within the last six month prior study; or a serum creatinine of more than 2 mg/dl prior study; pulmonary disorders or dyspnea of non-cardiac origin; or any malignancies.

Three groups of twelve patients receive a) a placebo, b) a low dose of human relaxin-2 at 10 µg/kg/d or c) high doses of relaxin at 100 µg/kg/d for a period of three months, including 4 weeks of a follow-up monitoring. The study is being done at one hospital, double-blind, prospective and randomized.

The following additional evaluations are being done or have been contemplated:

Echocardiographic evaluation of the diastolic function (E/E', LAVI) following relaxin administration
Spiroergometry for assessing exercise capacity and associated restrictive factors
Measurement of serum NT-proBNP as "companion marker"
Measurement of circulating IL-6, IL-8, nitrotyrosine as inflammation and companion markers
Determination of collagen turnover (PINP, PIIINP, MMP-2, TIMP-4, PIIINP, MM P-8)
QOL and Dyspnea questionnaires
Evaluation of different modes of relaxin administration: s.c. oder i.v. (PLGA-Galenik).
Monitoring "Safety/Efficacy": day 7, 30, 60, 90 and 120

The invention claimed is:

1. A method of treatment of a subject afflicted of a chronic heart failure with preserved ejection fraction (HFPEF) and stiffening of the heart muscle together with a deficient phosphorylation of a cardiospecific titin, comprising an administration of a pharmaceutical composition comprising human relaxin-2molecules capable of binding to the relaxin receptor (RXFP1) present on fibroblasts, fibromyoblasts, endothelial cells, endocardial cells, and cardiomyocytes in the cardiac muscle to increase heart compliance and stroke volume and to lower the end-diastolic pressure of the left ventricle.

2. The method of claim 1 for treating the effects of a hypophosphorylation of the cardiospecific titin N2B.

3. The method of claim 1, wherein the pharmaceutical composition comprises the human relaxin-2 molecules in admixture with a pharmaceutically acceptable adjuvant, carrier, diluent or excipient for subcutaeneous application.

4. The method of claim 1, wherein the pharmaceutical composition is formulated as an emulsion (oil-in-water or water-in-oil) for delivery to the oral or gastrointestinal tract mucosa.

5. The method of claim 1, wherein the pharmaceutical composition comprises a delivery vehicle selected from among a micelle, inverse micelle, liposome, cubosome and a mixture thereof.

6. The method of claim 1, wherein the pharmaceutical composition comprises a mucoadhesive protein which is associated with the delivery vehicle via a chemical or physical bond, so that the composition adsorbs to the mucosa or is retained on a mucosal surface for effecting systemic delivery of the relaxin.

7. The method of claim 1, wherein said composition is for subcutaneous infusion administering human relaxin-2 at a rate in the range of 10 µg/kg/day to 1000 µg/kg/day.

8. The method of claim 7, wherein human relaxin-2 is administered at an infusion rate in the range of 30 µg/kg/day to 100 µg/kg/day.

9. The method of claim 1, wherein said subject is further renally impaired.

10. The method of claim 1, wherein said subject has a creatinine clearance in the range of 30 to 75 mL/min/1.73 m$^2$.

* * * * *